United States Patent [19]

Adwers et al.

[11] Patent Number: 5,735,827
[45] Date of Patent: Apr. 7, 1998

[54] NEEDLE ASSEMBLY HAVING LOCKING ENCLOSURE

[75] Inventors: James Adwers, Wyckoff; Richard L. Griffith, Allendale, both of N.J.

[73] Assignee: Becton, Dickinson and Company, Franklin Lakes, N.J.

[21] Appl. No.: 721,511

[22] Filed: Sep. 26, 1996

[51] Int. Cl.[6] .................................................. A61M 5/32
[52] U.S. Cl. ............................................ 604/263; 604/192
[58] Field of Search ................................ 604/263, 187, 604/192, 110, 198

[56] References Cited

U.S. PATENT DOCUMENTS

| | | | |
|---|---|---|---|
| 3,840,008 | 10/1974 | Noiles | 128/221 |
| 4,735,618 | 4/1988 | Hagen | 604/192 |
| 4,790,828 | 12/1988 | Dombroski et al. | 604/198 |
| 4,795,443 | 1/1989 | Permenter et al. | 604/198 |
| 4,826,490 | 5/1989 | Byrne et al. | 604/198 |
| 4,850,977 | 7/1989 | Bayless | 604/198 |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,886,503 | 12/1989 | Miller | 604/192 |
| 4,887,998 | 12/1989 | Martin et al. | 604/110 |
| 4,898,589 | 2/1990 | Dolgin et al. | 604/198 |
| 4,911,706 | 3/1990 | Levitt | 604/198 |
| 4,950,250 | 8/1990 | Haber et al. | 604/192 |
| 5,092,851 | 3/1992 | Ragner | 604/192 |
| 5,108,379 | 4/1992 | Dolgin et al. | 604/198 |
| 5,242,417 | 9/1993 | Paudler | 604/192 |
| 5,348,544 | 9/1994 | Sweeney et al. | 604/192 |

*Primary Examiner*—John D. Yasko
*Attorney, Agent, or Firm*—John L. Voellmicke

[57] ABSTRACT

A shield assembly is provided for a needle cannula of a hypodermic syringe. The shield assembly includes inner and outer shield. The inner shield includes a guard selectively movable between a proximal position which permits use of needle cannula and a distal position which safely covers the tip of the needle cannula. The outer shield is frictionally and removably positioned over the needle cannula when the inner shield is in its proximal position. Movement of the inner shield to its distal shielding position enables alignment of cooperating locking structure on the inner shield and outer shield with one another for permanently securely locking the outer shield over the needle cannula.

12 Claims, 5 Drawing Sheets

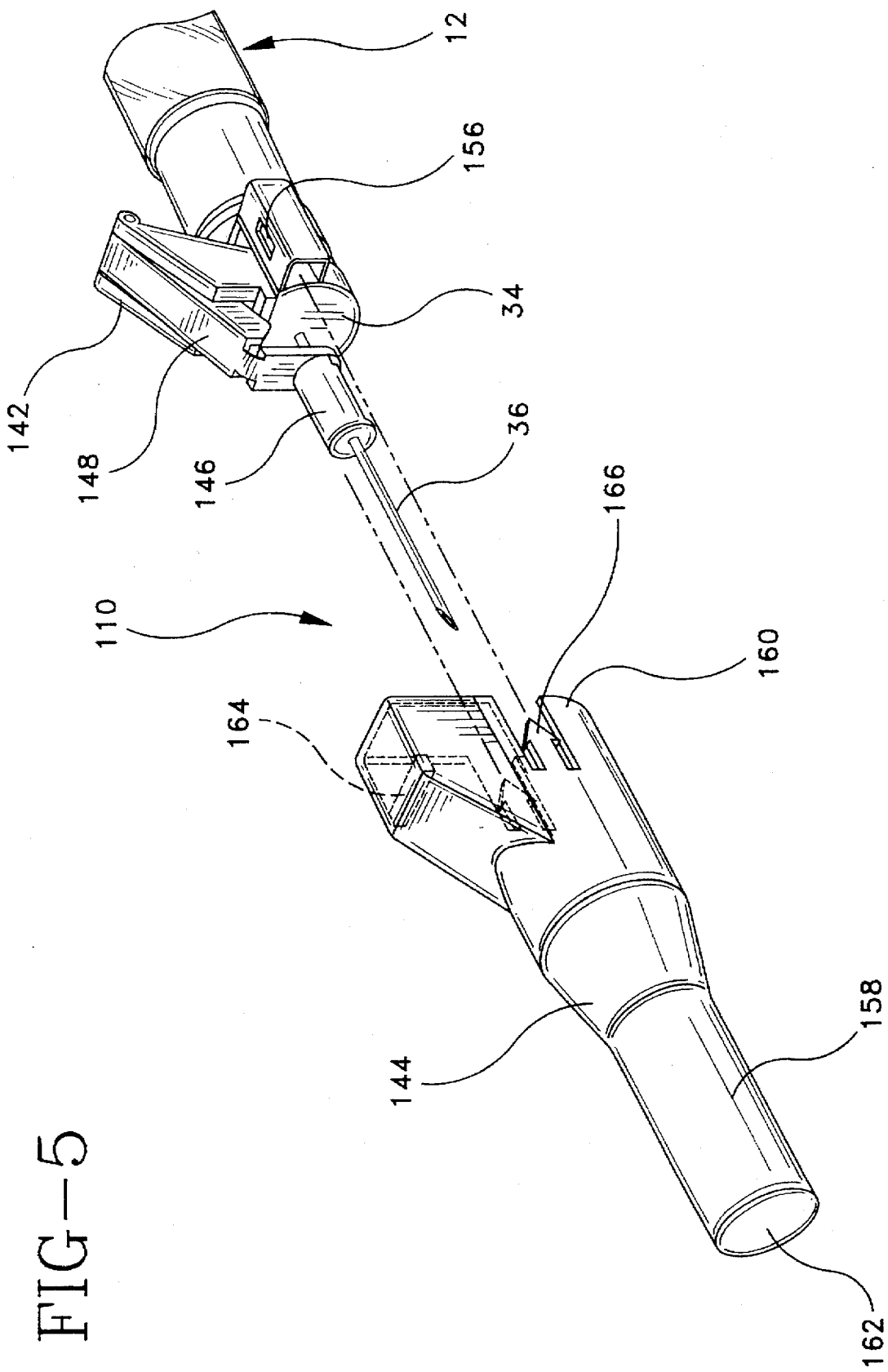

5,735,827

1

NEEDLE ASSEMBLY HAVING LOCKING ENCLOSURE

BACKGROUND OF THE INVENTION

1. Field of the Invention

The subject invention relates to shields for protectively enclosing a needle cannula both before and after use.

2. Description of the Prior Art

Most prior art hypodermic syringe assemblies have a cap-like safety shield telescoped over the needle cannula prior to use. Proximal portions of the safety shield may be frictionally retained on a needle hub. The syringe assembly is placed in condition for use by merely removing the cap-like safety shield.

A used needle cannula may carry infectious materials. As a result, the used needle cannula should be shielded and properly disposed of. Sharps receptacles are provided in most health care facilities for safe disposal of used hypodermic syringes. However, health care workers may not have the opportunity to bring the syringe to the nearest sharps receptacle immediately after use. Accordingly, being able to safely reshield the needle and protect the user from incidental contact with the needle between the time of use and proper disposal is desirable.

Prior art structures for shielding a used needle cannula have taken many forms. One form involves replacing the cap-like safety shield that had been removed to initially expose the needle cannula. This prior art shielding technique is problematic in that the health care worker must hold the shield in one hand and the used hypodermic syringe in the other hand. The hands are then moved toward one another to shield the used needle cannula. Misalignment or sudden movement of either hand can cause the accidental stick that this prior art shield is intended to avoid. Additionally, the health care worker may not have two free hands available immediately after completing an injection. Thus, the health care worker may deposit the unshielded needle on a nearby surface with the intention of completing the shielding later. The used needle cannula remains a safety hazard in this unshielded condition. Furthermore, many prior art safety shields are removable and enable unauthorized reuse of the potentially infectious needle cannula.

Express Mail TB617096029US (1)

The prior art also includes rigid tubular shields that are telescoped over the syringe barrel. These prior art shields are maintained in a proximal position on the syringe barrel while the hypodermic syringe is being used. The tubular shield may then be moved distally to surround the used needle cannula. These prior art safety shields are desirable in that shielding can be completed without placing a hand in front of the used needle cannula. However, these prior art shields require two-handed use. As noted above, health care workers may not have both hands free immediately after completing an injection.

Still other prior art safety shields include a tip guard that is slidably movable along a needle cannula from a proximal position where the tip of the needle cannula is exposed to a distal position where the guard safely encloses the pointed tip of the needle cannula. The tip guard may be connected to the needle hub by linkage that prevents complete removal of the guard from the needle cannula. The linkage or tip guard may be actuated by a thumb or forefinger on the hand holding the syringe barrel. Prior art shields of this type enable one-handed actuation without placing a hand in front of the used needle cannula. Thus, the needle cannula can be

2 safely shielded even in situations where the health care worker does not have two free hands available. The safely shielded syringe assembly may subsequently be discarded in an appropriate sharps receptacle. A hypodermic syringe assembly of this general type is shown, for example, in U.S. Pat. No. 5,348,544.

Despite the advantages of the above described prior art shields, the inventors herein have recognized the potential for still further improvements. For example, the above referenced tip guard leaves portions of the needle cannula proximally of the tip exposed and capable of being contacted. Also, the tip guard and the linkages between the tip guard and the needle hub are small and can be broken or cut. Thus, a person intent on the unauthorized reuse of a hypodermic syringe assembly can separate the tip guard from the linkage to re-expose the needle cannula for an unauthorized second use. Additionally, it would be desirable to provide a degree of shielding that would protect the needle cannula almost as well as it is protected in a sharps receptacle. It is also desirable to provide a degree of shielding that may not require the used needle assembly to be discarded in a sharps receptacle.

SUMMARY OF THE INVENTION

The subject invention is directed to a shield assembly for use with an elongate needle cannula having opposed proximal and distal ends. The shield assembly includes an inner shield having a guard that is movable along the needle cannula from a proximal position to a distal position. The guard is configured and dimensioned to permit use of the needle cannula when the guard is in its proximal position. However, movement of the guard to the distal position safely encloses the distal end of the needle cannula. The inner shield may further include linkage to prevent movement of the guard beyond the distal end of the needle cannula. The linkage may have one end connected to the guard and an opposed end connected to the needle hub or to the syringe barrel. The linkage may further be operative to propel the inner shield distally from its proximal position in response to digitally directed forces exerted thereon.

The shield assembly of the subject invention further comprises an outer shield. The outer shield is releasably engageable over the needle cannula when the inner shield is in its proximal position. However, the outer shield is permanently lockable over the needle cannula after the inner shield has been moved to its distal position. For example, linkage connecting the inner shield to the needle hub may prevent the outer shield from being moved into a locked position when the inner shield is in its proximal position. However, movement of the inner shield distally may realign the linkage and permit the outer shield to be permanently locked over the needle cannula.

The shield assembly provides several desirable features. For example, the inner shield may be single handedly activatable to provide effective shielding of the distal tip of the needle cannula immediately after the needle cannula has been used. The outer shield may then be telescoped in a proximal direction over the safely shielded needle cannula to provide a more complete and effective shielding that prevents contact with any portion of the used needle cannula and that effectively helps prevent unauthorized reuse of the needle cannula. Furthermore, the outer shield may be sufficiently strong to permit discarding of the redundantly shielded syringe in a receptacle other than a sharps receptacle.

BRIEF DESCRIPTION OF THE DRAWINGS

FIG. 5 is an exploded perspective view of an alternate shield assembly.

DETAILED DESCRIPTION OF THE PREFERRED EMBODIMENTS

Figure 1:
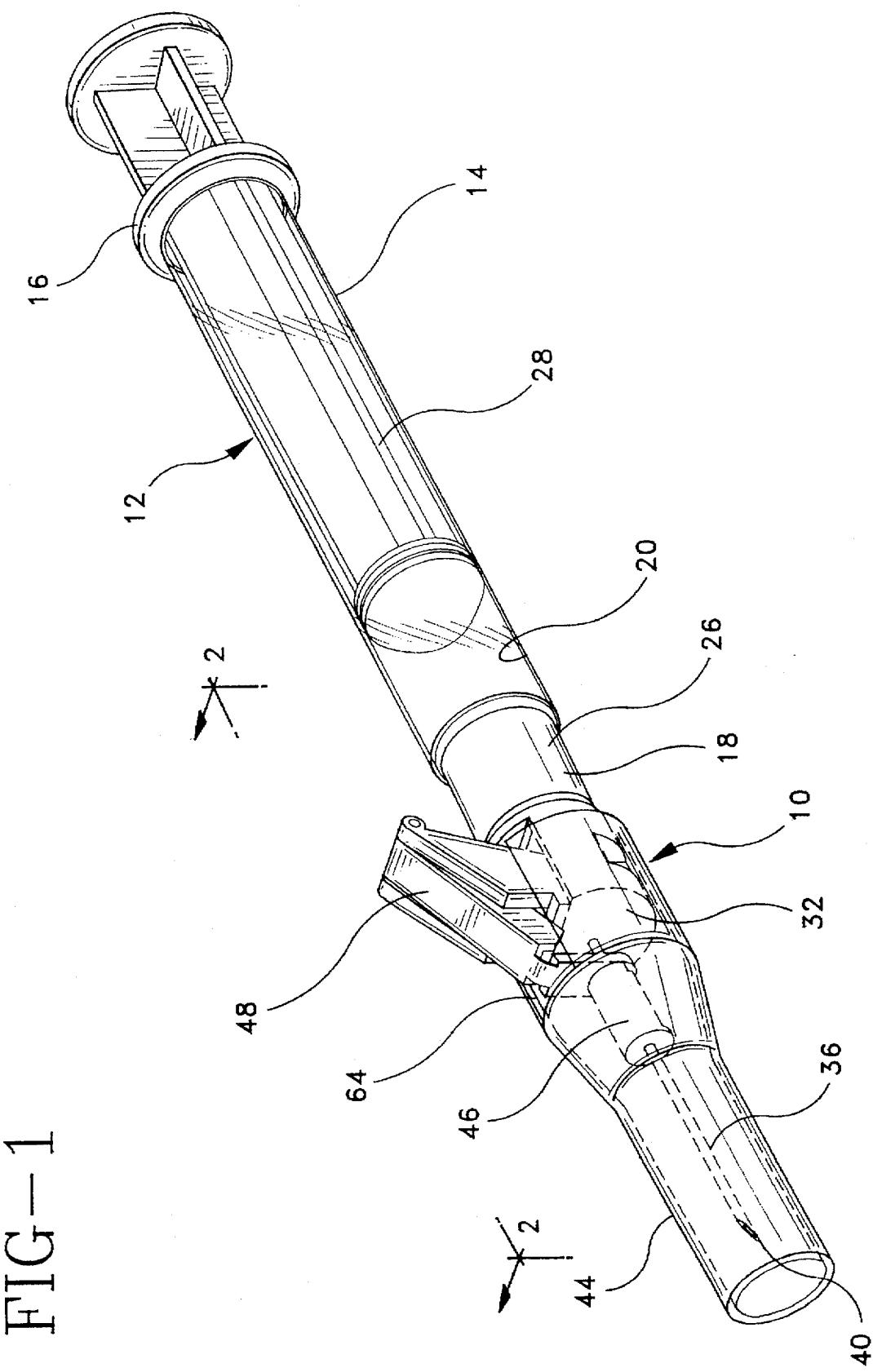
FIG. 1 is a perspective view of a fully shielded hypodermic syringe assembly.

A shield assembly in accordance with the subject invention is identified generally by the numeral 10 in FIGS. 1-4. Shield assembly 10 is used with a hypodermic syringe assembly 12. Syringe assembly 12 includes a tubular syringe barrel 14 having an open proximal end 16, an opposed distal end 18 and a fluid receiving chamber 20 therebetween. A tip 22 is defined at distal end 18 and includes a passage 24 which communicates with fluid receiving chamber 20. A luer collar 26 surrounds tip 20 and includes an array of internal threads. Syringe assembly 12 also includes a plunger 28 slidably disposed in fluid receiving chamber 20. Movement of plunger 28 urges fluid through passage 24 of tip 22 into or out of fluid receiving chamber 22.

Syringe assembly 12 further includes a needle assembly 32. Needle assembly 32 includes a hub 34 threadedly engaged with luer collar 26. Needle assembly 32 further includes a needle cannula 36 having a proximal end 38 securely affixed in hub 34 and an opposed sharply pointed distal end 40. A lumen extends continuously through needle cannula 36 and communicates with passage 24 through tip 22.

Shield assembly 10 comprises an inner shield assembly 42 and an outer shield 44. Inner shield assembly 42 includes a guard 46, an articulated arm array 48 and a clip 50. Articulated arm array 48 connects guard 46 to hub 34 of needle assembly 32. Articulated arm array 48 is preferably unitarily molded from a thermoplastic material and has hinge lines at selected locations. Opposed ends of articulated arm array 48 are securely connected to guard 46 and hub 34 respectively. However, at least one end of articulated arm array 48 can be unitarily molded with guard 46 and/or needle hub 34.

Figure 2:
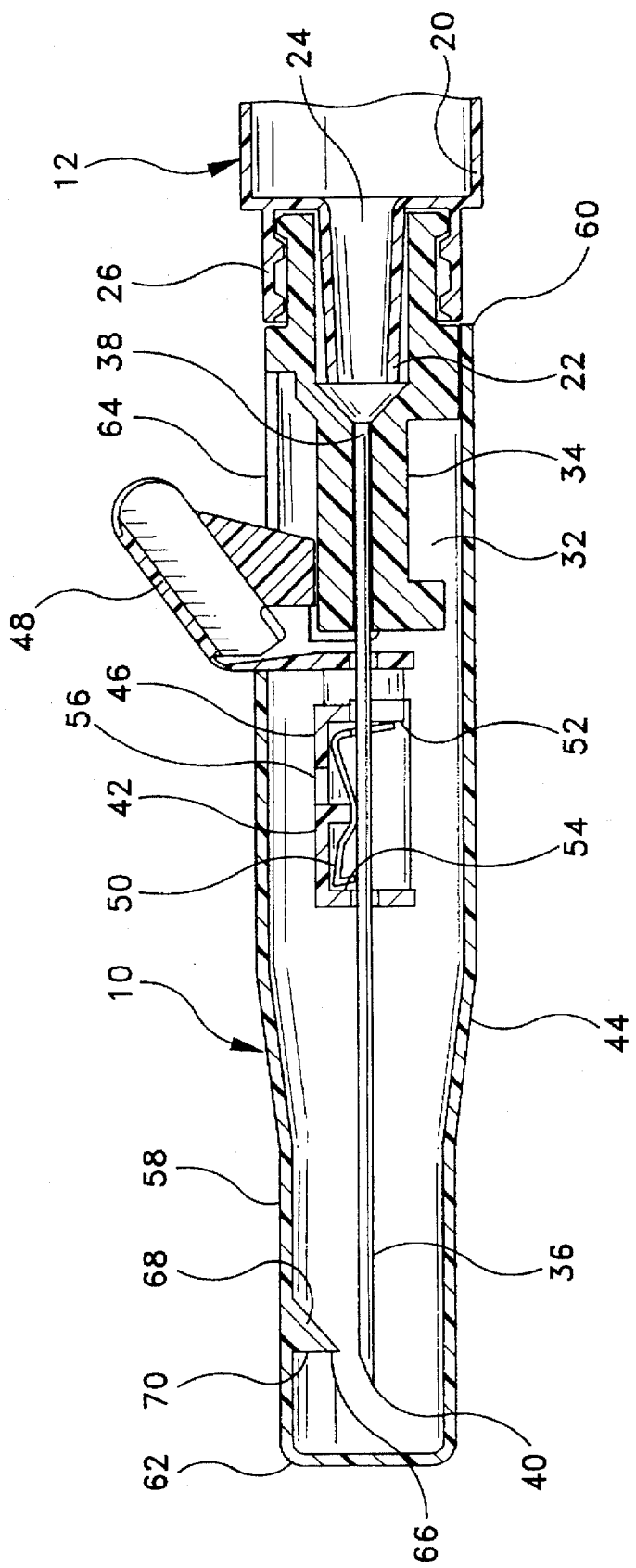
FIG. 2 is a cross-sectional view taken along line 2—2 in FIG. 1
Figure 3:
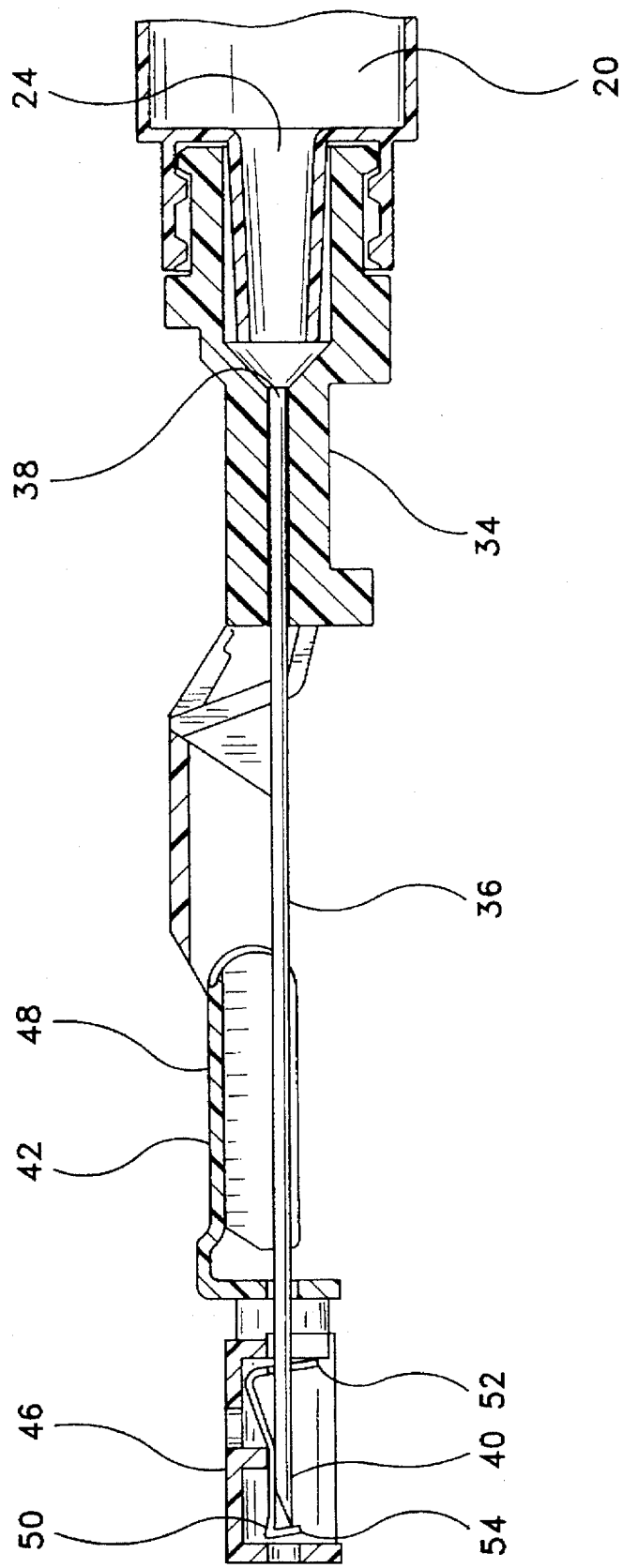
FIG. 3 is a cross-sectional view similar to FIG. 2, but showing the inner shield in its shielding disposition.

Clip 50 preferably is formed from a metallic material with opposed proximal and distal ends 52 and 54 respectively. Proximal end 52 of clip 50 includes an aperture through which needle cannula 36 is passed. Distal end 54 of clip 50 is bent and is biased against needle cannula 36 by guard 46. Guard 46 is formed with a locking aperture 56 at an intermediate location therealong. As shown in FIGS. 1 and 2, the various elements of articulated arm array 48 are collapsed on one another such that guard 46 and clip 50 are at a proximal position along needle cannula 36 and substantially adjacent hub 34.

Outer shield 44 is preferably unitarily molded from a plastic material and includes a generally tubular side wall 58, an open proximal end 60 and a closed distal end 62. Open proximal end 60 of outer shield 44 includes a notch 64 dimensioned to closely receive and surround articulated arm array 48. Additionally, open proximal end 60 is dimensioned and configured to closely frictionally engage portions of hub 34 and inner shield assembly 42. However, oppositely directed forces enable efficient separation of outer shield 44 from inner shield assembly 42 and hub 34 to expose needle cannula 36.

Outer shield 44 is provided with a locking tang 66 projecting inwardly at a location intermediate proximal and distal ends 60 and 62. Locking tang 66 includes a ramped proximal face 68 aligned at an acute angle to the longitudinal axis of outer shield 44 and a distal face 70 orthogonally aligned to the longitudinal axis. Locking tang 66 is preferably aligned with notch 64. Thus locking tang 66 also aligns with locking aperture 56 in guard 46 when notch 64 engages articulated arm assembly 48. As shown most clearly in FIG. 2, locking tang 66 on outer shield 44 is spaced distally from locking aperture 56 when guard 46 is in the proximal position. This spaced disposition of locking tang 66 from guard 46 ensures that outer shield 44 is retained on inner shield assembly 42 and hub 34 only by the above referenced frictional engagement.

Hypodermic syringe assembly 12 can be used by merely pulling outer shield 44 distally with sufficient force to separate outer shield 44 from inner shield assembly 42 and hub 34. Separation of outer shield 44 leaves distal portions of needle cannula 36 exposed and permits conventional use of hypodermic syringe assembly 12.

After using hypodermic syringe assembly 12, distally directed digital forces are exerted on articulated arm array 48 to urge guard 46 and clip 50 distally along needle cannula 36. Sufficient distal movement will position portions of guard 46 distally beyond distal tip 40 of needle cannula 36. Distal end 54 of clip 50 will then resiliently move toward an undetected or less deflected condition and into covering protective relationship on distal tip 40 of needle cannula 36. In this position, as shown most clearly in FIG. 3, distal tip 40 of needle cannula 36 is protectively covered, and accidental sticks are positively prevented. However, portions of needle cannula 36 proximally of cap 46 are exposed and can be contacted. Additionally, articulated arm array is small and can be broken or disabled by a person intent on using hypodermic syringe assembly 12 again for some unauthorized and/or illegal purpose.

Figure 4:
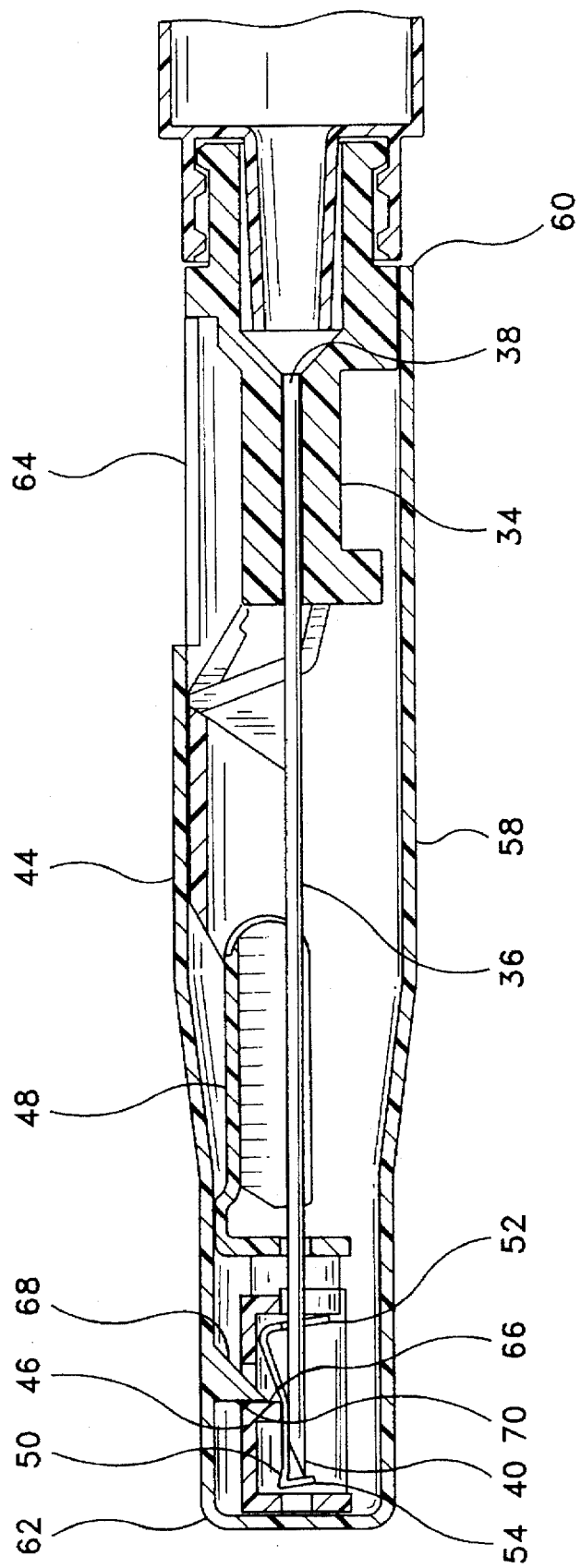
FIG. 4 is a cross-sectional view similar to FIG. 3, but showing the outer shield lockingly engaged over the used needle cannula.

Needle cannula 36 can be further protected against contact and unauthorized use by merely mounting outer shield 44 over distally positioned guard 46 and needle cannula 36. This distal to proximal movement of outer shield 44 over used needle cannula 36 is substantially risk free in view of the effective shielding of distal tip 40 achieved by guard 42 and clip 50 of inner shield assembly 42. Proximal movement of outer shield 44 urges ramped proximal face 68 of locking tang 66 into engagement with distally positioned guard 46 of inner shield assembly 42. Guard 46 and outer shield 44 will deflect slightly to permit further proximal movement of outer shield 44. However, after sufficient proximal movement of outer shield 44, locking tang 66 will align with locking aperture 56. Guard 46 and outer shield 44 will then resiliently return toward an undetected condition such that locking tang 66 positively engages in locking aperture 56 as shown in FIG. 4. Orthogonally aligned locking face 70 of locking tang 66 will engage guard 46 and prevent removal of outer shield 44 from inner shield assembly 42. Hence, accidental contact with proximal portions of used needle cannula 36 are prevented and unauthorized reuse of hypodermic syringe assembly 12 is substantially prevented. Additionally, as noted above, outer shield assembly 44 is structurally strong and rigid. Thus, disposal of the redundantly shielded hypodermic syringe in a receptacle other than a sharps receptacle will be safe and may be permitted by certain governmental jurisdictions.

FIG. 5 shows an alternate shield assembly 110. Shield assembly 110 is used with hypodermic syringe assembly 12 as described above and illustrated in the preceding figures. Shield assembly 110 comprises an inner shield assembly 142 and an outer shield 144. Inner shield assembly 142 is substantially identical to the above described inner shield assembly 42. In particular, inner shield assembly 142 includes a guard 146, an articulated arm array 148 connecting guard 146 to needle hub 34, and a clip 150 secured in guard 146 and biased against needle cannula 34. Guard 146 differs from guard 46 described above and illustrated in FIGS. 1–4 in that a locking aperture need not be provided. Rather, portions of inner shield assembly 142 adjacent hub 34 are formed to include locking apertures 156.

Outer shield 144 includes a rigid generally tubular side wall 158, an open proximal end 160 and a closed distal end 162. Portions of outer shield 144 adjacent proximal end 160 include an inwardly directed stop wall 164. Outer shield 144 further includes locking pawls 166 dimensioned and disposed to align with locking apertures 156 on inner shield assembly 142. The relative dispositions of stop wall 164 and locking pawls 166 are significant in assuring efficient cooperation between inner shield assembly 142 and outer shield 144. In particular, stop wall 164 is disposed to contact articulated arm array 148 when articulated arm array 148 is in the collapsed condition shown in FIG. 6. This engagement between stop wall 164 and articulated arm array 148 prevents outer shield 144 from being moved proximally a sufficient distance for pawls 166 to engage locking apertures 156. Thus, when outer shield assembly 142 is in the proximal position shown in FIG. 6, outer shield 144 can only be frictionally and releasably engaged on hub 34 and on portions of inner shield assembly 142. However, movement of guard 146 to the distal position substantially linearly aligns the elements of articulated arm array 148, and thereby reduces the transverse dimensions of inner shield assembly 142. Stop wall 164 will not engage the extended articulated arm array 148. Hence, outer shield 144 can be moved proximally a sufficient distance for locking pawls 166 to lockingly engage locking apertures 156 for substantially preventing separation of outer shield 144 from inner shield assembly 142 and from hypodermic syringe assembly 12.

What is claimed is:

1. A shield assembly for a needle cannula, said needle cannula having a proximal end securely connected to a hub and an opposed distal end, said shield assembly comprising:
   an inner shield having a guard slidably movable along said needle cannula from a proximal position where said distal end of said needle cannula is exposed, to a distal position where said guard protectively covers at least said distal end of said needle cannula; and
   an outer shield dimensioned and configured for releasably shielding substantially all of said needle cannula when said guard of said inner shield is in said proximal position, said outer shield having at least one lock dimensioned and disposed for substantially permanently locking said outer shield over said needle cannula when said guard of said inner shield is moved to said distal position.

2. The shield assembly of claim 1, wherein said guard of said inner shield includes a locking portion, said lock of said outer shield being spaced distally from said locking portion of said guard when said guard is in said proximal position, and said lock of said outer shield being lockingly engageable with said locking portion of said guard when said guard of said inner shield is moved to said distal position.

3. The shield assembly of claim 2, wherein the locking portion of said guard includes a locking aperture formed therein, said lock of said outer shield including a locking tang dimensioned and disposed for engagement in said locking aperture of said guard when said guard is in said distal position.

4. The shield assembly of claim 3, wherein said inner and outer shields include alignment means for ensuring alignment of said lock of said outer shield with said locking aperture of said guard.

5. The shield assembly of claim 1, wherein said inner shield comprises an articulated arm array connecting said guard to said needle hub, said outer shield including a stop wall dimensioned and disposed for contacting said articulated arm array when said guard of said inner shield is in said proximal position for preventing said lock of said outer shield from permanently locking said outer shield around said needle cannula.

6. The shield assembly of claim 5, wherein said articulated arm array defines a major transverse dimension when said guard is in said proximal position and a minor transverse dimension when said guard is in said distal position, said minor transverse dimension of said articulated arm array being sufficiently less than said major cross-sectional dimension for preventing contact between said lock of said outer shield and said articulated arm array and for permitting said outer shield to be moved into a position where said lock substantially permanently locks said outer shield over said needle cannula.

7. A shieldable needle assembly comprising:
   a needle hub;
   a needle cannula having a proximal end securely connected to said needle hub and an opposed distal end spaced from said needle hub;
   an inner shield assembly comprising a guard slidably engaged with said needle cannula and movable from a proximal position substantially adjacent said needle hub, to a distal position substantially enclosing said distal end of said needle cannula, said inner shield assembly further comprising an articulated arm array having a proximal portion connected to said needle hub and a distal portion connected to said guard, said articulated arm array being selectively extendable for preventing distal movement of said guard beyond said needle cannula; and
   an outer shield releasably engageable over said needle cannula and said guard when said guard is in said proximal position, and being substantially permanently engaged over said needle cannula and said guard when said guard is in said distal position.

8. The assembly of claim 7, wherein said outer shield includes a locking tang projecting inwardly thereon, said tang being disposed to lockingly engage said guard when said guard is in said distal position.

9. The assembly of claim 8, wherein said guard includes a locking aperture, said tang of said outer shield being disposed to engage in said locking aperture when said guard is in said distal position.

10. The assembly of claim 9, wherein said outer shield includes opposed proximal and distal ends, said proximal end of said outer shield including a notch dimensioned for slidably receiving said articulated arm array therein, said notch and said arm being disposed relative to one another such that receipt of said articulated arm array in said notch aligns said tang with said locking aperture of said guard.

11. The assembly of claim 7, wherein said needle hub includes at least one locking portion formed thereon, said outer shield including at least one resiliently deflectable locking pawl selectively engageable with said locking portion on said hub.

12. The assembly of claim 11, wherein said articulated arm assembly defines a major transverse dimension when said guard is in said proximal position and a minor transverse dimension when said guard is in said distal position, said major transverse dimension of said articulated arm array preventing movement of said outer shield into a position where said pawl of said outer shield engage said locking portion on said needle hub.

\* \* \* \* \*